US008659418B2

(12) United States Patent
Kreml

(10) Patent No.: US 8,659,418 B2
(45) Date of Patent: Feb. 25, 2014

(54) DEVICES AND METHODS FOR BEHAVIOR ASSESSMENT AND MODIFICATION

(76) Inventor: Stephanie Sue Ling Kreml, Southlake, TX (US)

( * ) Notice: Subject to any disclaimer, the term of this patent is extended or adjusted under 35 U.S.C. 154(b) by 359 days.

(21) Appl. No.: 13/029,821

(22) Filed: Feb. 17, 2011

(65) Prior Publication Data

US 2011/0199205 A1 Aug. 18, 2011

Related U.S. Application Data

(60) Provisional application No. 61/305,921, filed on Feb. 18, 2010.

(51) Int. Cl.
*G08B 1/08* (2006.01)
*G08B 23/00* (2006.01)
*G09B 19/00* (2006.01)

(52) U.S. Cl.
USPC .............. 340/539.11; 340/539.12; 340/573.1; 340/573.2; 434/127; 128/920; 128/921

(58) Field of Classification Search
None
See application file for complete search history.

(56) References Cited

U.S. PATENT DOCUMENTS

| | | | | |
|---|---|---|---|---|
| 4,218,611 A | * | 8/1980 | Cannon | 377/20 |
| 5,908,301 A | * | 6/1999 | Lutz | 434/236 |
| 6,473,368 B1 | * | 10/2002 | Stanfield | 368/107 |
| 6,513,532 B2 | * | 2/2003 | Mault et al. | 600/595 |
| 6,558,165 B1 | | 5/2003 | Curry et al. | |
| 7,210,240 B2 | * | 5/2007 | Townsend et al. | 33/512 |
| 7,855,936 B2 | * | 12/2010 | Czarnek et al. | 368/10 |
| 2006/0197670 A1 | * | 9/2006 | Breibart | 340/573.1 |
| 2008/0137486 A1 | * | 6/2008 | Czarenk et al. | 368/9 |
| 2010/0194573 A1 | * | 8/2010 | Hoover et al. | 340/573.1 |
| 2010/0245077 A1 | * | 9/2010 | Shmueli et al. | 340/539.1 |

OTHER PUBLICATIONS

Amft et al, "On-Body Sensing Solutions for Automatic Dietary Monitoring," 2009 IEEE, pp. 62-70.

Dong et al, "A Device for Detecting and Counting Bits of Food Taken by a Person During Eating,", BIBM, 2009, IEEE International, Nov. 1, 2009, 4 pgs.

Zhang, et al., "Detection of Activities by Wireless Sensors for Daily Life Surveillance: Eating and Drinking," Sensors Mar. 3, 2009, pp. 1499-1517.

* cited by examiner

*Primary Examiner* — Julie Lieu

(57) ABSTRACT

In one embodiment, a behavior assessment and modification device comprises a strap for fastening the device about a user's limb; a data interface for receiving input by the user; a sensor for detecting movement by the user; a processor for processing movement data detected by the sensor and interpreting the movement data according to the input received from a user; a memory component for storing the input received from the user, the movement data, and the interpretations of the movement data; and a signaling component for alerting the user according to the processed movement data.

18 Claims, 4 Drawing Sheets

DEVICES AND METHODS FOR BEHAVIOR ASSESSMENT AND MODIFICATION

CLAIM OF PRIORITY

This application claims priority of prior provisional Application Ser. No. 61/305,921 filed Feb. 18, 2010, the entire contents of which are incorporated herein by reference.

FIELD OF THE APPLICATION

The present patent disclosure relates generally to behavior assessment devices, and more particularly, and not by way of any limitation, to devices and methods for behavior assessment and modification.

BACKGROUND AND SUMMARY

Many behaviors are undesirable, and often persons participating in undesirable behaviors would like to be able to change them, or may be unaware of the severity of the undesirable behavior. One such undesirable behavior is overeating, which is detrimental to an individual's health and well-being. Such individuals generally know they should eat less, but do have an effective tool to modify the undesirable behavior.

Currently, some methods available for persons desiring to modify an undesirable behavior generally involve self-monitoring of food intake such as point counting, diet diaries, and various other calorie-counting related methods. While such methods have been used numerous times in research studies, these methods rely completely on self-reporting, which inherently can be unreliable and therefore ineffective. For example, diet diary applications on "smart" phones and personal digital assistants have been helpful by being readily available and providing databases of nutrition information, but unless an individual accurately reports and or remembers their food intake, these methods are limited by the inherent problems of under reporting and/or false reporting.

In accordance with the present disclosure invention there are presented devices and methods for behavior assessment and modification which overcome the foregoing difficulties.

BRIEF DESCRIPTION OF THE DRAWINGS

A more complete understanding of the present invention may be had by reference to the following Detailed Description when taken in connection with the accompanying Drawings, wherein.

DETAILED DESCRIPTION OF THE DRAWINGS

The present patent disclosure is broadly directed to a behavior assessment and modification device that is electronic, wearable, monitors certain behaviors, and provides real-time feedback to a user so that an undesirable behavior can be modified. The user wearing the behavior assessment and modification device needs only to initially set up the device and thereafter wear the device accordingly for the device to be effective in alerting the user regarding the undesirable behavior. The main components consist of a data interface, a sensor, a processor, a memory component, and a signaling component. When the user is wearing the device, the user's behavior is linked to a specific action that can be monitored. These actions can then be interpreted to provide the user with real-time feedback. The device may also be configured to interface with an external computer to give more detailed feedback to the user such that the user may reconfigure settings based on the feedback and/or revised goals based on the feedback. Based on the goals of the user, the processor can be programmed to detect actions tied to the behavior the user would like to change and to provide real-time feedback to the user via the signaling component.

In one aspect, an embodiment of a behavior assessment and modification device may comprise a strap for fastening the device about a user's limb; a data interface for receiving input by the user; a sensor for detecting movement by the user; a processor for processing movement data detected by the sensor and interpreting the movement data according to the input received from a user; a memory component for storing the input received from the user, the movement data, and the interpretations of the movement data; and a signaling component for alerting the user according to the processed movement data. In one embodiment, the device may be removably mounted into a receiving compartment incorporated into the strap.

In another aspect, an embodiment of a behavior assessment and modification device, the data interface may comprise a wireless communication system for negotiating with an external computer having a user interface. In yet another embodiment, the data interface may comprise a removable memory card. In still another embodiment, the data interface may comprise a port configured to receive a data cable for connecting with and interfacing data with an external computer.

In yet another aspect, a method for assessing and modifying a certain behavior may comprise receiving input from a user into a behavior assessment and modification device; using the received input to calculate a maximum number of bites per meal; sensing movement by the user; interpreting movement data from the user's movements and determining that the user is taking bites; and alerting the user when the maximum number of bites is reached.

Figure 1A:
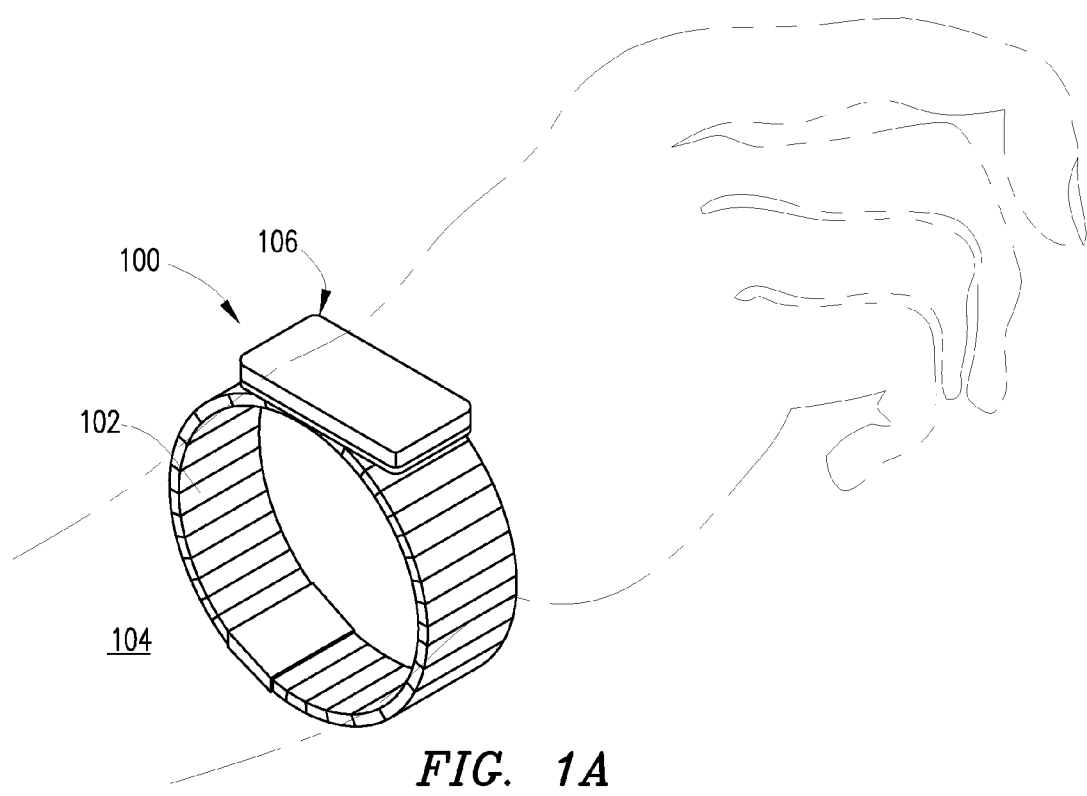
FIG. 1A is a perspective view of one embodiment of a behavior assessment and modification device according to the present disclosure.

Referring now to the Drawings, and particularly to FIG. 1A thereof, there is shown a behavior assessment and modification device 100 according to one aspect of the present disclosure. The device comprises a strap 102 for wearing the device 100 about a user's limb, such as wrist 104. Coupled to the strap 102 is a module 106 housing functional components of the device 100 therein. A user inputs data into the module 106 via a user interface. According to the data input by the user, a maximum number of bites is calculated for the user. As movement is sensed through the day, a processor within module 106 interprets the data to determine whether a meal has begun. If a meal has begun, the movement data is interpreted and when the user approaches the maximum number of bites for the meal, a signal component such as an actuator is activated to signal to the user that the maximum number of bites has been reached. Likewise, the user may elect to receive an alert before the maximum limit is reached so the user can plan the remainder of the meal accordingly.

In one embodiment, strap 102 is a decorative strap and the module 106 appears as a decorative feature such that persons other than the user may perceive the device 100 merely as a decorative bracelet or other similar wearable item. Accordingly, the strap 102 may comprise a link bracelet similar to a watch, fashioned from metals, leather, and other durable goods known to those skilled in the art as suitable for constructing items worn about a user's wrist or ankle.

Figure 1B:
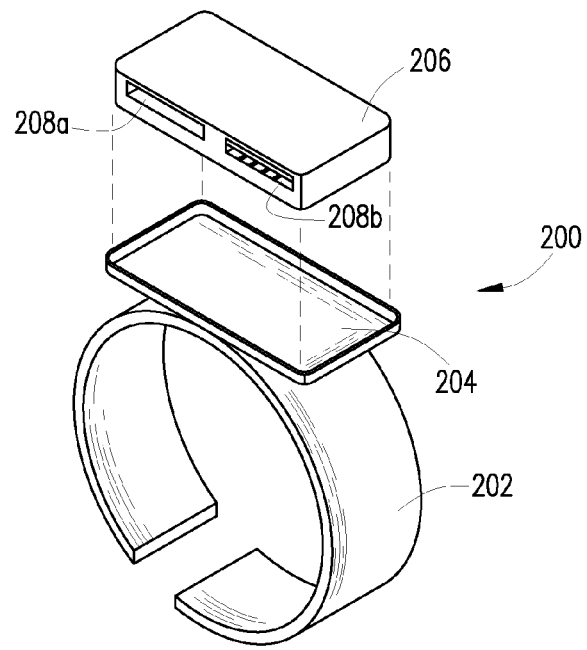
FIG. 1B is a perspective view of another embodiment of a behavior assessment and modification device according to the present disclosure.

Referring now to FIG. 1B, there is shown another embodiment of a behavior assessment and modification device 200 according to another aspect of the present disclosure. The device 200 comprises a strap 202 having a housing 204 coupled thereto. Removably coupled with housing 204 is a module 206 for housing various functional components of device 200. Module 206 may couple into housing 204 by various ways, including, but not limited to, a snap fit, a slide fit, a tension fit, fasteners which may fasten above or onto sides of housing 204, a cover which fits over module 206, and various other fastening methods known to those skilled in the art. As shown in FIG. 1B, module 206 may comprise various data interfaces 208a and 208b for receiving and negotiating data between external sources, such as, for example, an external computer whereupon the user may input, view, and manipulate data collected by device 200 in order to achieve certain goals of a behavior modification process. Data interface 208a is shown as a receptacle for receiving a removable memory card such as a flash memory card such as a secure digital (SD) memory card or other similar removable memory card which may transfer data between device 200 and an external computer, and likewise may also serve as a memory component of device 200. Data interface 208b is shown as a plug for receiving a data cable such as a USB or other suitable data cable for transferring data between the device 200 and an external computer and may also be used as a recharging port to recharge a power source within device 200. As shown in FIG. 1B, strap 202 may be configured as a cuff-style bracelet or other similarly fashioned wrist wear.

Figure 1C:
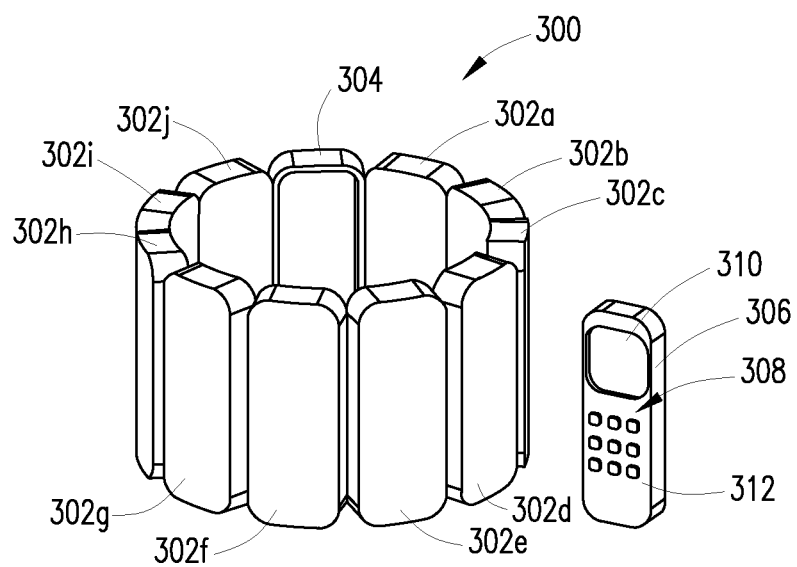
FIG. 1C is a perspective view of another embodiment of a behavior assessment and modification device according to the present disclosure.
Figure 1D:
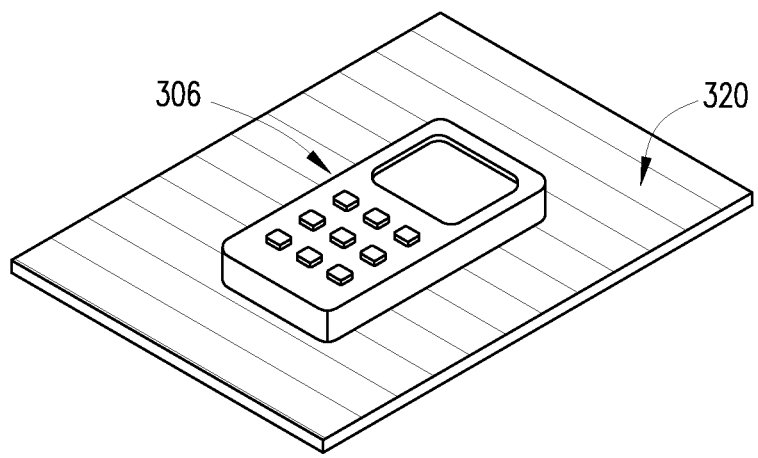
FIG. 1D is an illustration of another aspect of the behavior assessment and modification device according to FIG. 1C.

Referring to FIGS. 1C and 1D, there is shown another embodiment of a behavior assessment and modification device 300 according to another aspect of the present disclosure. Device 300 comprises multiple planks 302a-302j coupled together which together with receiving plank 304 form a bracelet strap for wearing device 300 about a user's wrist. Module 306 is removably coupled into receiving plank 304. Module 306 accordingly comprises various functional components of device 300. As shown in FIG. 1C, module 306 may comprise a user interface 308 directly on one surface thereof. User interface 308 may comprise a screen 310 and a keypad 312 enabling a user to directly input data and interface with device 300.

As shown in FIG. 1D, module 306 may be placed onto a charging mat 320 which may serve both to charge a power source within module 306, but may also be enabled with a wireless communication system, including, but not limited to a short-range communication system such as BLUETOOTH®, ZIGBEE®, or other suitable short-range technology known to those skilled in the art. Such a charging mat 320 enabling wireless interface would enable a user of device 300 to both charge the device and update data settings within the device 300 simply by removing the module from the plank 304 and letting module 306 rest on the charging mat for a certain period of time, such as overnight. Accordingly, such minimal effort required by the user may ensure that the user will continue using device 300 in a manner that is effective for achieving a behavior modification goal.

Figure 2A:
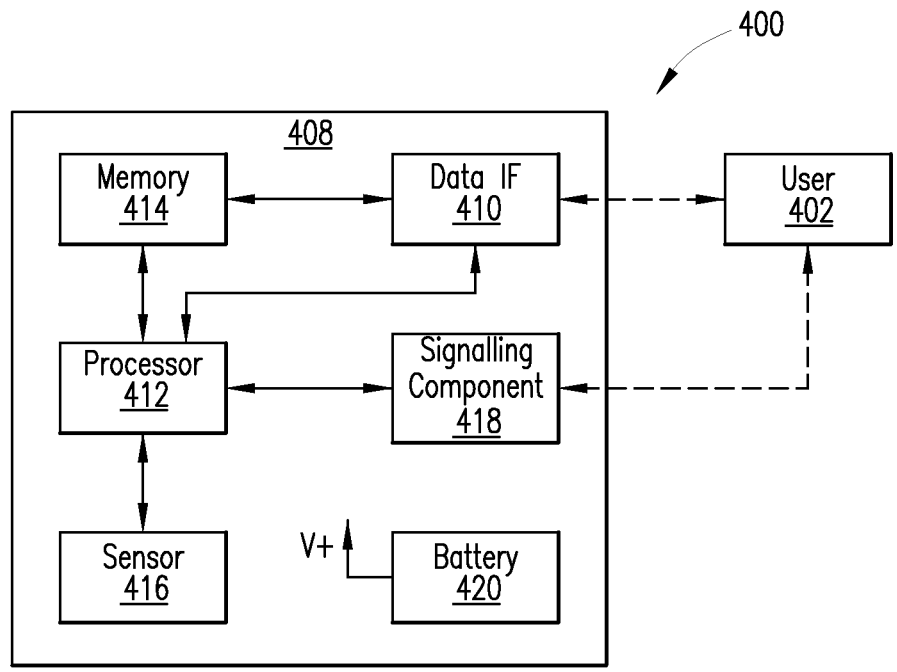
FIG. 2A is a diagram illustrating pertinent components of a behavior assessment and modification device according to one embodiment of the present disclosure.

Referring now to FIG. 2A, there is shown a diagram illustrating pertinent components of a behavior assessment and modification device 400 according to one embodiment of the present disclosure. Device 400 comprises a module 408 which may comprise pertinent functional components of device 400. Module 408 comprises a data interface 410 for receiving and interfacing data with a user 402. In one embodiment, data interface 410 may comprise a user-interface for direct entry onto device 400 by user 402. Data interface 410 may also comprise a removable memory card, such as an SD or similar removable memory card known to those skilled in the art.

Data interface 410 receives data from user 402 into module 410 and thereafter interfaces with processor 412 and memory component 414. Processor 412 controls overall operation of device 400 and interacts with device subsystems such as data interface 410, memory component 414, sensor 416, signaling component 418, and various other subsystems that may be utilized by device 400. Operating system software and other device specific software used by processor 412 may be stored in a persistent store of memory component 414, which may be a read-only memory (ROM) or similar storage element or alternatively into a temporary volatile store such as read-access memory (RAM). Device 400 is generally battery-powered and therefore includes battery 420. Battery 420 provides electrical power to most if not all electrical circuitry in device 400. Battery 420 is coupled to a regulator (not shown) which provides power V+ to all of the circuitry in device 400. In some embodiments, battery 420 may be rechargeable, may be a kinetic battery which is recharged by movement, or be a suitable alternative power source similar to those used in certain watches and other power sources known to those skilled in the art of wearable wrist devices.

Processor 412 interfaces with sensor 416 for interpreting movement data collected by sensor 416. In one embodiment, sensor 416 may comprise a tri-axis accelerometer that when strapped to the user's wrist, can measure acceleration in three axes as the user moves his or her arm. However, sensor 416 may comprise any other type of inertial sensor that measures a physical quantity and converts it into a signal that can be processed, such as gyroscopes, quartz rate sensors, magneto-hydrodynamic sensors, etc. Signally component 418 is preferably an actuator such as a pager motor with an offset weight that creates vibration when rotated, but may comprise other devices or materials capable of creating a tactile sensation to provide feedback in real-time to user 402, such as electroactive polymers, piezoelectric materials, electrostatic devices, and other suitable signaling devices known to those skilled in the art. Accordingly, various sensory alerts may be utilized for signaling user 402 in real-time. For example, in addition to a tactile alert, in some embodiments signaling component 418 may further comprise a light-emitting diode (LED) or other similar light source for providing a visual alert in conjunction with a tactile alert, or in some embodiments, in place of a tactile alert. Likewise, in some embodiments, signaling component 418 may emit an audio signal in addition to, or in place of a tactile alert. According to settings determined by user 402, processor 412 communicates with signaling component 418 to signal user 402 upon the happening of certain events.

Such events will be discussed, infra, in more detail, but may include a signal indicating a bite limit has been reached, when a user needs to take additional bites or begin a meal, or when user 402 is participating in other behaviors that user 402 would like to assess or modify.

Figure 2B:
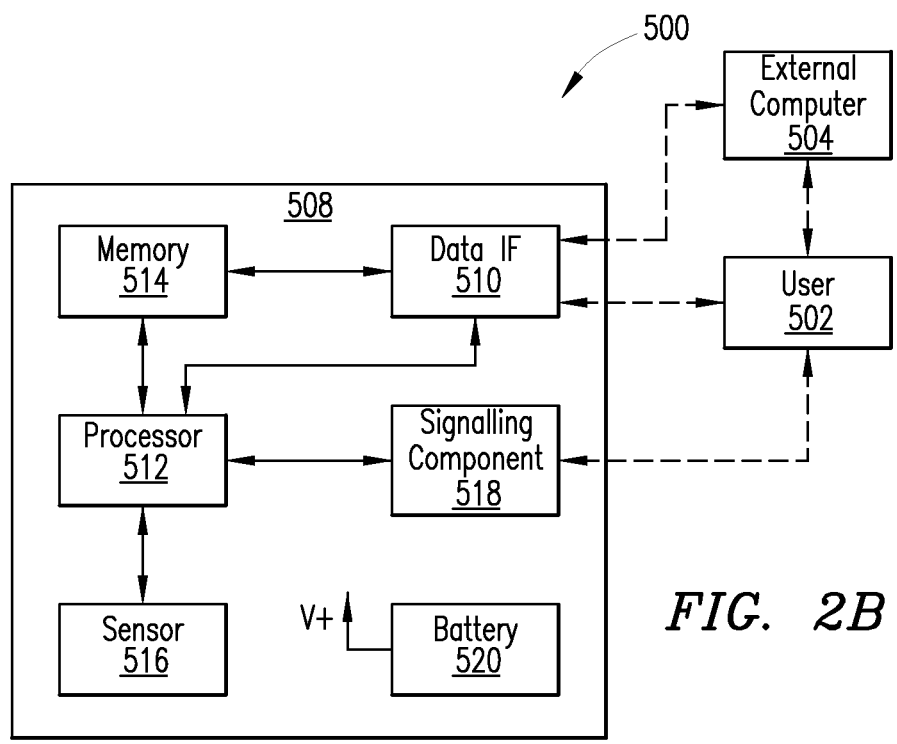
FIG. 2B is a diagram illustrating pertinent components of a behavior assessment and modification device according to another embodiment of the present disclosure.

Referring now to FIG. 2B, there is shown a diagram illustrating pertinent components of a behavior assessment and modification device 500 according to another embodiment of the present disclosure. Device 500 comprises module 508 which may comprise pertinent functional components of device 500. Accordingly, the functional components comprising module 508 such as processor 512, memory component 514, sensor 516, signaling component 518, and battery 520 are similar in scope and function to similar components shown and described in conjunction with device 400 hereinabove.

Data interface 510 of device 500 may be configured to interface with external computer 504. External computer 504 may comprise various types of computing devices, including, but not limited to a desktop computer system, computer network system, smart phone, portable computing device such as a laptop, netbook, tablet computer, and various other fixed or portable computer systems. Data interface 510 may comprise a data cable, such as a USB or other suitable cable, for connecting directly with external computer 504, or may comprise a wireless communication system for negotiating with external computer 504. The wireless communication system may comprise a short-range communication system such as may comprise BLUETOOTH®, ZIGBEE®, or any other suitable short-range technology that can be implemented for purposes of the present patent disclosure. Accordingly, user 502 may interface with external computer 504 to view and interpret data collected from device 500, and/or re-adjust goals and settings for device 500.

Some embodiments may comprise various other equipment connected with device 500 and/or external computer 504, either by a network connection, data cable, or wirelessly. For example, a scale (not shown) for receiving user's 502 weight may interface with device 500 and/or external computer. Other equipment which may be connected may include monitoring equipment such as a blood pressure monitor, heart rate monitor, and various other monitoring equipment which may be helpful in user 502 achieving a desired behavior modification goal. Similarly, the device 500 may be linked with a global positioning system (GPS) such that not only can the processor 512 interpret the user's movements, but may also consider the user's location in conjunction with the movement. For example, the GPS may detect and communicate that user 502 was at Restaurant A for a certain amount of time. The device may accordingly be able to correlate certain menu items from Restaurant A with movement data to provide better feedback to the user in achieving the desired behavior modification.

In order to properly set up and program device 500, certain input is necessary from the user. Preferably, user 502 may wear device 500 during an initial evaluation period during which user 502 may participate in general daily activities. Sensor 516 accordingly collects movement data which is interpreted by processor 512 according to an algorithm for interpreting movement data to distinguish a bite taking movement versus walking, taking a drink, and various other motions experienced by user's wrist during a day. After the evaluation period, user 502 receives feedback from device 500 regarding the number of bites taken during certain periods of a day, including, but not limited to meal times. The data taken and interpreted during the evaluation period is preferably combined with other user provided data inputs. Such input may comprise various factors, including amount of exercise; physical features such as age, weight, gender, and height; and a target or goal weight or another intended behavior modification goal. The foregoing data is then used to determine the user's basal metabolic rate (BMR), preferably using the Harris-Benedict Equation. The Harris-Benedict equation applied is as follows:

BMR (kcal) for a male=66+(6.23×weight in pounds)+ (12.7×height in inches)−(6.76×age in years)

BMR (kcal) for a female=655+(4.35×weight in pounds)+(4.7×height in inches)−(4.7×age in years)

Other equations which may be used include the Mifflin-St. Jeor formula, the Katch-McArdle formula, the Cunningham formula, and various other formulas known to those skilled in the art. The Harris-Benedict Principle is then applied to determine the recommended daily caloric intake to reach the target or goal weight. As an alternative to the Harris-Benedict Principle, data from sensor 516 may be interpreted to assess the user's activity level. Accordingly, a person's daily caloric need is adjusted according to their BMR and their exercise level. A sample chart related to the Harris-Benedict Principle is shown below relating certain multipliers to BMR per exercise level to calculate daily caloric intake requirements:

| Amount of Exercise | Daily Caloric Requirement |
| --- | --- |
| Little to none | BMR × 1.2 |
| Light (1-3 days per week) | BMR × 1.375 |
| Moderate (3-5 days per week) | BMR × 1.55 |
| Heavy (6-7 days per week) | BMR × 1.725 |
| Very heavy (2 × per day, extra heavy workouts) | BMR × 1.9 |

Accordingly, the user's BMR and daily caloric intake requirements may be calculated using software resident on the external computer 504, or software resident in memory component 514, wherein the BMR and caloric needs are calculated after inputting data into device 500.

Once the daily caloric intake requirement is determined, an algorithm then uses the user's target or goal weight to determine a bite count for each meal. For example, a 35 year old female, Female A, having worn device 500 for an evaluation period, weighs 137 pounds, is 66 inches tall, and does little exercise on a regular basis, would have a BMR of 1396 kcal as calculated by the Harris Benedict formula (BMR=655+ (4.35×137)+(4.7×66)−(4.7×35). Using the calculated BMR of 1396 kcal along with the multiplier for little exercise (BMR×1.2), Female A would require 1676 kcal per day.

Figure 3:
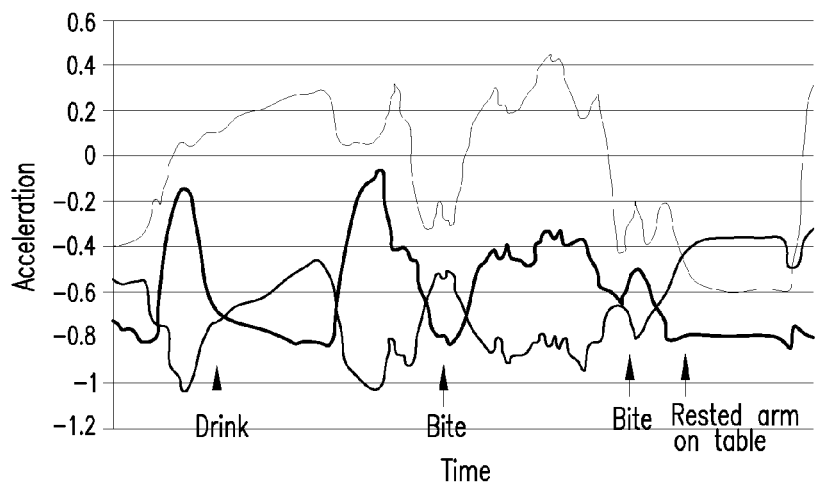
FIG. 3 is a diagram illustrating certain data elements collected in the operation of a behavior assessment and modification device according to the present disclosure.

Referring now to FIG. 3, there is shown a sample of data collected by one embodiment of a behavior assessment and modification device similar to device 500, wherein bites are determined based on movement versus time and acceleration. During the evaluation period during which Female A wore the device, the data collected by the device indicated that she takes approximately 50 bites per meal and eats three meals per day. Her estimated caloric density is approximately 11.2 kcal per bite (1676 kcal/(50 bites×3 meals)=11.2 kcal/bite). If Female A would like to lose one pound per week to achieve a target weight of 120 pounds, she will need to reduce her caloric intake by approximately 500 kcal per day (one pound equaling approximately 3500 kcal and dividing 3500 kcal by seven days to get 500 kcal per day) such that her new caloric intake for each day should be 1176 kcal, which translates into 35 bites per meal as a target goal (1176 kcal/day divided by 11.2 kcal/bite divided by 3 meals/day). As abruptly decreasing caloric intake can be uncomfortable and possibly lead to this dietary change not being sustainable, the algorithm would taper the number of bites from the user's baseline over a long period of time to the target goal. For example, the number of bites may be decreased by one for that particular meal each week, such that during the first week, the user is signaled to stop eating after the 49th bite, and during the second week the user is signaled after the 48th bite, etc. until the target goal is reached. This would allow the user's body to slowly adjust to decreasing levels of caloric intake with the goal of allowing the user to maintain these changes.

As shown in FIG. 3, the device is programmed to distinguish certain movements from other similar movements. For example, taking a bite and taking a drink involve similar motions, but take different amounts of time and require different acceleration. The algorithm is programmed accordingly to interpret and distinguish these motions.

Figure 4:
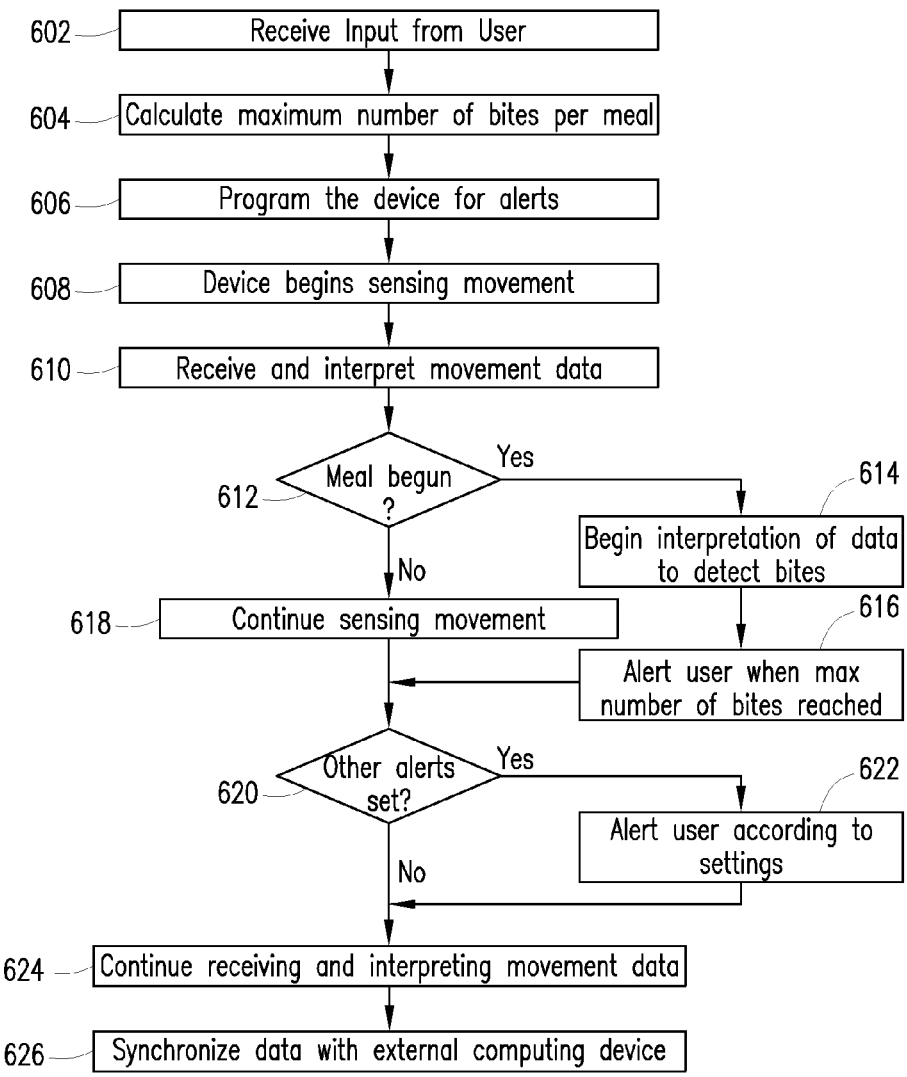
FIG. 4 is a flowchart illustrating one embodiment of a method of behavior assessment and modification according to the present disclosure.

Referring to FIG. 4, there is shown a flowchart illustrating one embodiment of a method of behavior assessment and modification according to the present disclosure. The method as shown in FIG. 4 may be utilized with any of the embodiments of a behavior assessment and modification device as shown in FIG. 1A-2B and described hereinabove in conjunction therewith. A user accordingly inputs data into the device 602, either directly or by using various methods of data interface as described previously herein. The input data may comprise various data elements including, but not limited to, weight, height, gender, activity level, BMR (if calculated previously, target or goal weight. Once the data is received, an algorithm can calculate a maximum number of bites per meal 604 in order for the user to achieve the desired weight goal. The processor is thereafter programmed 606 to communicate with the signaling component once the maximum number of bites is reached. Once setup of the device is complete, the device begins sensing movement 608 once the user fastens the device about their wrist. Upon sensing movement, the processor receives the movement data and begins interpretation of the data 610. If interpretation of the data indicates that a meal has begun 612, the data is further interpreted to detect and count the number of bites taken 614. The device then alerts the user once the maximum number of bites is reached 616. Upon completion of a meal, the device returns to sensing movement 618.

In some embodiments, the user may set additional alerts 620, including, but not limited to, an alert to eat a snack, an alert to begin another meal, or various other alerts that may be helpful to the user in achieving their weight loss/maintenance or other behavior modification goal. If such alerts are set for the device, the device alerts the user accordingly 622. Accordingly, after an alert or meal event, the device continues to receive and interpret data 624 throughout the remainder of the wearing period, such as, for example, a day.

Another aspect of the behavior assessment and modification device may be to provide feedback for other characteristics of the user's eating behavior that they would like to change. For example, if the user tends to eat too quickly, the device could alert the user via the signaling component to slow down. Or if the user would like to stop having afternoon snacks, the device could alert the user if the user starts to eat during a specific time of day.

The user may periodically connect the device to an external computer to obtain more feedback offline, including charts, graphs, tables, etc., about his or her behavior as well as to update the algorithm resident on the processor based on changes in data factors such as weight, new goals, etc. Additionally, the device could update the user's status via a social networking website, such as FACEBOOK® or TWITTER®, allowing the user to obtain support via contacts thereon. Another application of a behavior assessment and monitoring device could be in conjunction with various weight loss plans and pre-packaged food items wherein the prepackaged items may be equipped with a radio frequency identification tag (RFID) or other similar electronic tag and the device similarly equipped with a corresponding reader component for reading such electronic tags wherein the amount of bites for a user's meal may be re-calculated according to the prepackaged food item being consumed along with other food items that may be expected to be eaten along therewith.

Accordingly, there are numerous activities and behaviors that may be monitored using a behavior assessment and modification device according to the present disclosure. For example, the illustrated behavior assessment and modification device may be used to monitor smoking habits and help a user gain control over a smoking habit. The device may be programmed to interpret movements to detect when the user is smoking a cigarette. Accordingly, the device may signal the user to stop after inhaling a certain number of times and gradually decrease the number of inhales set for signaling until the user reaches a goal intake, which may include complete cessation.

Another example may include use by a person having certain metabolic or dietary restrictive condition such as hypoglycemia and/or diabetes. The device may be programmed to monitor a user's food intake according to times of the day and/or last meal consumed and signal a user if the user has not eaten in a certain amount of time and need to eat in order to maintain certain blood-sugar levels as directed by their physician. Similarly, the device may be used to monitor persons having eating disorders such as anorexia or bulimia to both monitor and assess behavior and provide real-time feedback when prohibited or undesirable motions occur, including detecting movements related to purging after a meal or limiting caloric intake.

Another exemplary use may be in conjunction with an elderly person or physically or mentally disabled person to monitor their caloric intake for the day. The device may be programmed to similarly signal a user of the need for a meal or if they have not taken enough bites. Likewise, the data interface may communicate with an external computer such that a caretaker may remotely monitor the user.

Another use may be to assess and modify other behavior disorders that involve repetitive movement such as trichotillomania, wherein a user is alerted in real-time when the sensor senses that the user is performing the repetitive motion of pulling or plucking hair. In some users, the sensor may also be programmed to sense an additional motion of eating hair after it has been pulled or plucked.

Although preferred embodiments of the present invention are illustrated in the accompanied drawings and described in the foregoing detailed description, it will be understood that the invention is not limited to the embodiments disclosed but is capable of numerous rearrangements, modifications and substitutions in parts and elements without departing from the spirit of the invention and the scope as set forth in the following claims.

Although the preferred embodiments are shown and described in conjunction with wearing an assessment and modification device about a user's wrist, other embodiments of the device may be fashioned and programmed for wearing about other parts of a user's body, such as an ankle or leg. Such exemplary uses may prove beneficial for physical therapy or similar uses for helping persons learning to walk or rehabilitation of certain leg movements. Similarly, the device may also be used for recreational or sports applications such as learning dance steps and the like, and if worn about the wrist, include used such as and various other recreational activities including bowling, tennis, football, and various other sporting activities which may benefit from monitoring and modifying a user's movements and behavior.

What is claimed is:

1. A behavior assessment and modification device comprising:
    a strap for fastening the device about a user's limb;
    a data interface, said data interface configured to:
        receive input by the user and calculating a maximum number of bites per meal, wherein the input comprises at least the user's age, weight, gender, and height;
        interface data with an external computer; and
        calculate an adjusted maximum number of bites after data is interfaced with the external computer;
    a sensor for detecting movement by the user;
    a processor for processing movement data detected by the sensor and interpreting the movement data according to the input received from a user;
    a memory component for storing the input received from the user, the movement data, and the interpretations of the movement data; and
    a signaling component for alerting the user when the adjusted maximum number of bites is reached according to the processed movement data.

2. The device according to claim 1 wherein the data interface comprises a wireless communication system for negotiating with the external computer.

3. The device according to claim 2 wherein the wireless communication system comprises a short-range enabled communication system.

4. The device according to claim 1 wherein the data interface and the memory component are embodied in a removable memory card for transferring data between the device and an external computer having a user interface.

5. The device according to claim 1 wherein the data interface comprises a port for receiving a data cable, wherein the data cable negotiates data between the device and an external computer having a user interface.

6. The device according to claim 1 wherein the data interface comprises a user interface for a user to input data directly into the device.

7. The device according to claim 1 wherein the device is removably mounted into a receiving compartment incorporated into the strap.

8. The device according to claim 1 wherein the signaling means comprises an actuator for providing a tactile alert to the user.

9. The device according to claim 8 wherein the actuator is a pager motor, an electroactive polymer, piezoelectric material, or an electrostatic device.

10. The device according to claim 1 wherein the strap is fastened about the user's wrist.

11. A method for assessment and modifying a certain behavior, the method comprising:
    receiving input from a user into a behavior assessment and modification device, the input comprising at least the user's age, weight, gender, and height;
    using the received input to calculate a maximum number of bites per meal;
    interfacing data with an external computer, wherein the maximum number of bites is adjusted after data is interfaced with the external computer;
    sensing movement by the user;
    interpreting movement data from the user's movements and determining that the user is taking bites; and
    alerting the user when the adjusted maximum number of bites is reached.

12. The method according to claim 11 wherein the data is interfaced with the external computer via a short-range enabled communication system.

13. The method according to claim 11 further comprising collecting data during an evaluation period, wherein the user wears the behavior assessment and modification device to collect preliminary data.

14. The method according to claim 11, wherein interpreting movement data from the user's movements comprises interpreting that another specified event requiring an alert to the user has begun and alerting the user of the specified event.

15. The method according to claim 11, further comprising detecting a certain food item that the user is consuming from a radio frequency identification tag located on the packaging of the food item and calculating the maximum number of bites according to input received from the user and data identified by the radio frequency identification tag.

16. The method according to claim 11 wherein the input is received from the user directly into a user interface module of the behavior assessment and modification device.

17. The method according to claim 11 wherein the behavior assessment and modification device is removably coupled with a strap fastened about the user's wrist.

18. The method according to claim 11 wherein the behavior assessment and modification device is removably coupled with a strap fastened about the user's ankle.

* * * * *